US009721730B1

(12) United States Patent
Muffoletto et al.

(10) Patent No.: US 9,721,730 B1
(45) Date of Patent: Aug. 1, 2017

(54) CAPACITOR HAVING MULTIPLE ANODES HOUSED IN A STACKED CASING

(71) Applicant: Greatbatch Ltd., Clarence, NY (US)

(72) Inventors: Barry C. Muffoletto, Alden, NY (US); Anthony C. Perez, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 15/449,111

(22) Filed: Mar. 3, 2017

(51) Int. Cl.
| H01G 9/008 | (2006.01) |
| H01G 9/02 | (2006.01) |
| H01G 9/035 | (2006.01) |
| H01G 9/042 | (2006.01) |
| H01G 9/10 | (2006.01) |
| H01G 9/052 | (2006.01) |
| H01G 9/145 | (2006.01) |

(52) U.S. Cl.
CPC .............. *H01G 9/008* (2013.01); *H01G 9/02* (2013.01); *H01G 9/035* (2013.01); *H01G 9/042* (2013.01); *H01G 9/0425* (2013.01); *H01G 9/052* (2013.01); *H01G 9/10* (2013.01); *H01G 9/145* (2013.01)

(58) Field of Classification Search
CPC .......... H01G 9/008; H01G 9/02; H01G 9/035; H01G 9/042; H01G 9/0425; H01G 9/052; H01G 9/10; H01G 9/145
USPC ......................................................... 361/517
See application file for complete search history.

(56) References Cited

U.S. PATENT DOCUMENTS

| 5,894,403 | A | 4/1999 | Shah et al. |
| 5,920,455 | A | 7/1999 | Shah et al. |
| 5,926,362 | A | 7/1999 | Muffoletto et al. |
| 6,219,222 | B1 | 4/2001 | Shah et al. |
| 6,224,985 | B1 | 5/2001 | Shah et al. |
| 6,334,879 | B1 | 1/2002 | Muffoletto et al. |
| 6,468,605 | B2 | 10/2002 | Shah et al. |
| 6,687,117 | B2 | 2/2004 | Liu et al. |
| 6,819,544 | B1 | 11/2004 | Nielsen et al. |
| 6,850,405 | B1 | 2/2005 | Stemen et al. |
| 7,012,799 | B2 | 3/2006 | Muffoletto et al. |
| 7,072,171 | B1 | 7/2006 | Muffoletto et al. |

(Continued)

*Primary Examiner* — Eric Thomas
*Assistant Examiner* — Michael P McFadden
(74) *Attorney, Agent, or Firm* — Michael F. Scalise

(57) ABSTRACT

A capacitor is described. The capacitor comprises a first casing member having a first face wall extending to a first surrounding sidewall in turn extending to a first annular edge defining a first open end. A second casing member has a second face wall extending to a second surrounding sidewall in turn extending to a second annular edge defining a second open end. The second casing member is supported on the first annular edge to thereby close the first open end of the first casing member and provide a first capacitor enclosure comprising the first and second casing members in a stacked relationship. A cover is secured to the second annular edge to close the second casing member and provide a second capacitor enclosure. An anode, for example of tantalum, and a cathode active material, for example of ruthenium oxide, reside in capacitive association with each other inside each of the first and second capacitor enclosures. A working electrolyte is also contained in the capacitor enclosures. Finally, leads extend from each anode through insulative seals structures supported by the casing members for making electrical connection to the capacitor.

15 Claims, 3 Drawing Sheets

(56) References Cited

U.S. PATENT DOCUMENTS

| | | |
|---|---|---|
| 7,085,126 B2 | 8/2006 | O'Connor et al. |
| 7,092,242 B1 | 8/2006 | Gloss et al. |
| 7,116,547 B2 | 10/2006 | Seitz et al. |
| 7,483,260 B2 | 1/2009 | Ziarniak et al. |
| 8,027,149 B2 | 9/2011 | Hahl et al. |
| 8,086,312 B2 | 12/2011 | Norton et al. |
| 9,312,075 B1 | 4/2016 | Liu et al. |
| 2003/0090857 A1 | 5/2003 | Liu et al. |
| 2005/0243501 A1* | 11/2005 | Muffoletto ............... H01G 9/06 361/534 |
| 2008/0151474 A1* | 6/2008 | Ziarniak ................ H01G 4/35 361/529 |

* cited by examiner

CAPACITOR HAVING MULTIPLE ANODES HOUSED IN A STACKED CASING

FIELD OF THE INVENTION

The present invention relates to capacitors, more particularly, to a casing structure designed to house at least two anodes for an electrolytic capacitor.

SUMMARY OF THE INVENTION

As more and more medical applications are investigated and implemented to aid and assist the human body, devices needed to deliver the desired therapy are becoming increasingly more sophisticated, both functionally and in terms of their structural makeup. Modern implantable devices require power sources that are relatively small in size, but powerful enough to meet the therapy requirements. For example, a cardiac defibrillator has a battery powering circuits performing such functions as, for example, the heart sensing and pacing functions. This requires electrical current of about 1 microampere to about 100 milliamperes. From time-to-time, the cardiac defibrillator may require a generally high rate, pulse discharge load component that occurs, for example, during charging of a capacitor assembly in the defibrillator for the purpose of delivering an electrical shock to the heart. The electrical shock is for the purpose of treating a tachyarrhythmia, the irregular, rapid heartbeats that can be fatal if left uncorrected. Treating a tachyarrhythmia requires electrical current of about 1 ampere to about 4 amperes.

The current trend in medicine is to make cardiac defibrillators, and like implantable devices, as small and lightweight as possible without compromising their power. This, in turn, means that the components within the capacitor, particularly the anode, need to be constructed to optimum energy density and volumetric efficiency parameters.

The present invention is, therefore, directed to a novel casing design for a capacitor. The capacitor casing houses at least two anodes in a volumetrically efficient design comprising a first casing member having a first face wall extending to a first surrounding sidewall in turn extending to a first annular edge defining a first open end. A second casing member has a second face wall extending to a second surrounding sidewall in turn extending to a second annular edge defining a second open end. The second casing member is supported on the first annular edge to thereby close the first open end of the first casing member and provide a first capacitor enclosure comprising the first and second casing members in a stacked relationship. A cover is secured to the second annular edge to close the second casing member and provide a second capacitor enclosure.

A cathode active material, for example, ruthenium oxide is in electrical contact with at least one of the first face wall and the second face wall inside the first capacitor enclosure, and at least one of the second face wall and the cover inside the second capacitor enclosure. Further, at least one anode resides in each of the first and second capacitor enclosures facing the cathode active material. Capacitor anodes typically comprise an anode active material such as tantalum, aluminum, or niobium. There is also a separator intermediate the anode and cathode in both of the first and second capacitor enclosures.

Electrical connection to the capacitor is made through a first insulative seal supported by the first casing member and a second insulative seal supported by at least one of the second casing member and the cover. The insulative seals electrically insulate a respective first lead for the first anode housed in the first capacitor enclosure and a second lead for the second anode housed in the second capacitor enclosure from the casing serving as a terminal for the cathode active material.

Finally, a working electrolyte is provided in the first and second capacitor enclosures in contact with the first and second anodes and the cathode active material.

These and other objects of the present invention will become increasingly more apparent to those skilled in the art by reference to the following detailed description and the appended drawings.

DETAILED DESCRIPTION OF THE PREFERRED EMBODIMENTS

Figure 1:
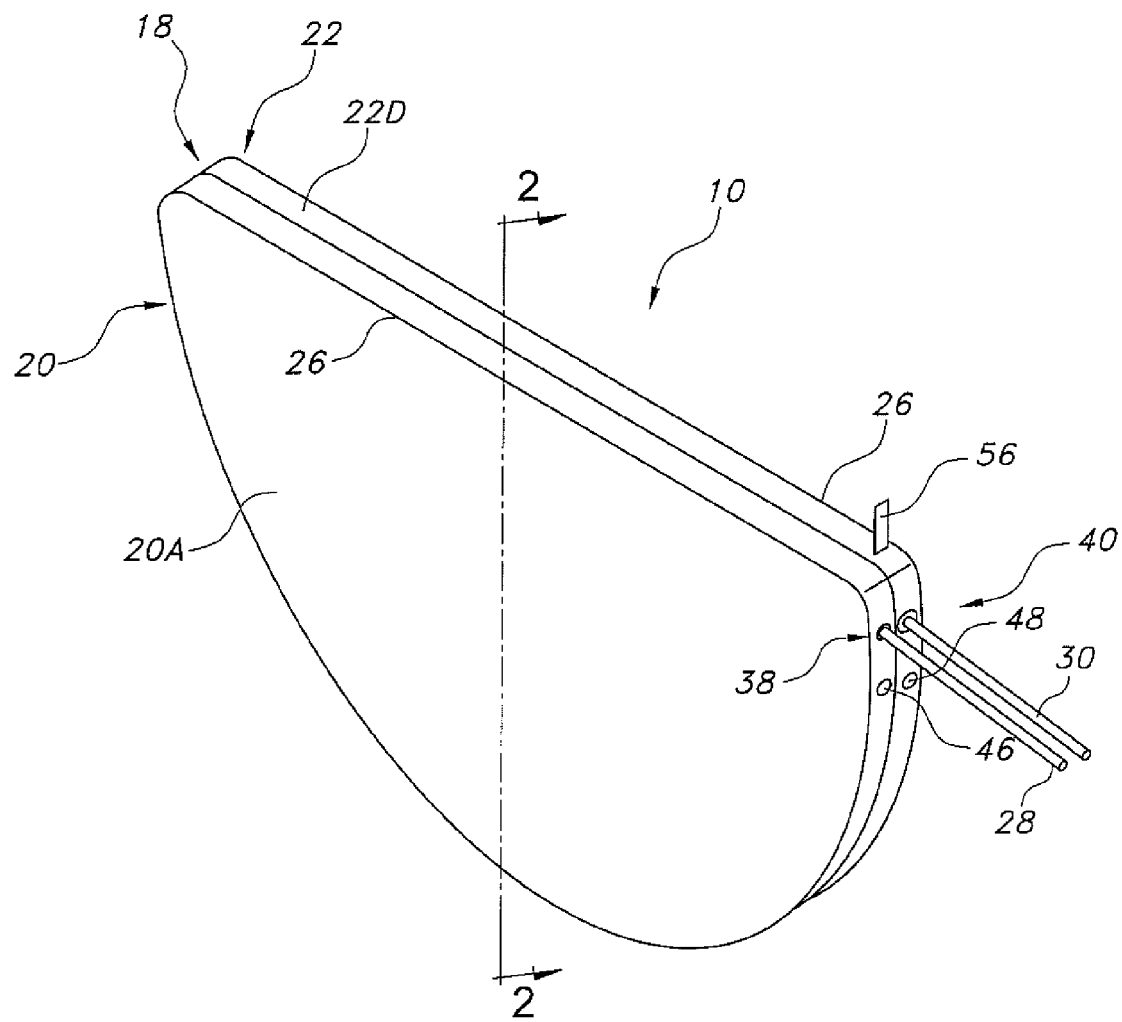
FIG. 1 is a perspective view of an exemplary capacitor 10 according to the present invention.
Figure 2:
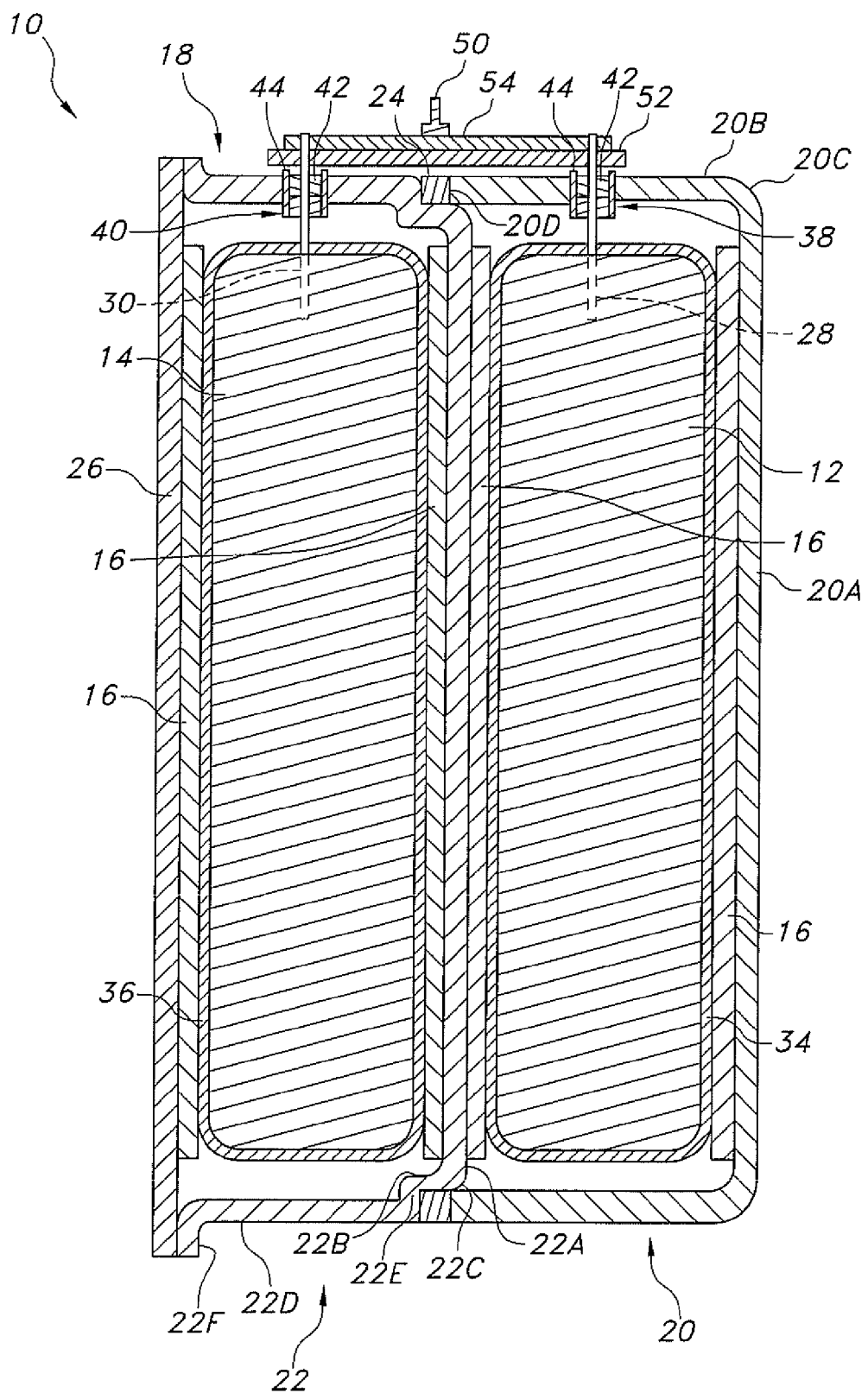
FIG. 2 is a cross-sectional view taken along line 2-2 of FIG. 1 illustrating a dual anode design with each anode housed in a respective capacitor enclosure.

Referring now to the drawings, an exemplary capacitor 10 according to the present invention is illustrated in FIGS. 1 and 2. As will be described in detail hereinafter, capacitor 10, is well suited for implantable cardiac device capacitor applications and comprises a first anode 12 of a first anode active material, a second anode 14 of a second anode active material, and a cathode of a cathode active material 16 housed inside a hermetically sealed casing 18. Preferably, the side-by-side first and second anodes 12, 14 are of the same active material. The capacitor 10 can be of either an electrochemical type with the anode and the cathode being provided by conductive substrates having a capacitive material contacted thereto or, an electrolytic type with the cathode being provided by a conductive substrate having capacitive properties and the anode being of a valve metal. The illustrated capacitor 10 is preferably of the latter type, however, that should not be construed as limiting. The capacitor electrodes are operatively associated with each other by a working electrolyte (not shown) contained inside the casing 18.

Exemplary casing 18 is of metal material comprising first and second casing members 20 and 22 in the general shape of clamshells stacked one partially inside the other. For example, the casing members can be shallow-drawn, formed by metal injection molding, or by machining a block of suitable metal, among other techniques. Suitable conductive metals for the casing members 20, 22 are selected from the group consisting of tantalum, titanium, nickel, niobium, stainless steel, aluminum, zirconium, and mixtures and alloys thereof. Regardless the metal, the casing members 20, 22 have a thickness of about 0.015 to about 0.5 millimeters and serve as one terminal or contact for making electrical connection between the capacitor 10 and its load.

In particular, the first casing member 20 comprises a face wall 20A joined to a surrounding or annular sidewall 20B by an intermediate annular curved sidewall 20C. Sidewall 20B extends to an annular upper edge 20D defining an open end for the first casing member 20.

The second casing member 22 is shaped differently and comprises a face wall 22A joined to a minor surrounding or annular sidewall 22B by a first annular curved sidewall 22C.

The minor surrounding sidewall 22B is joined to a major surrounding or annular sidewall 22D by an outwardly extending annular step 22E. The major surrounding sidewall 22D extends to an outwardly projecting annular rim 22F defining an open end for the second casing member 22.

The annular step 22E between the minor and major surrounding sidewalls 22B, 22D of the second casing member 22 is sized and shaped to receive the upper edge 20D of the first casing member 20 stacked therein. The first and second casing members 20, 22 fitted together in this manner are secured to each other by an annular weld 24, preferably a laser weld, residing at the respective upper edge 20D and the outwardly extending annular step 22E. When stacked and secured together, the second casing member 22 closes the open end of the first casing member 20 with the respective sidewalls 22D and 20B substantially aligned with each other.

A cover plate 26 serving as a lid is supported on the outwardly projecting annular rim 22F of the second casing member 22 to thereby close the open end of the second casing member 22 and consequently close the casing 18. While not shown in the drawing, the cover 26 is secured to the second clamshell casing member 22 by a weld, which is preferably a laser weld.

The first anode 12 is housed in the first capacitor enclosure formed by the first casing member 20 closed by the stacked second casing member 22. Similarly, the second anode 14 is housed in the second capacitor enclosure formed by the second casing member 22 closed by the cover plate 26. The active material of the anodes 12 and 14 is typically of a metal in the form of a pellet. The anode metal is selected from the group of valve metals consisting of tantalum, aluminum, titanium, niobium, zirconium, hafnium, silicon, and mixtures thereof. As is well known by those skilled in the art, the anode metal in powdered form, for example tantalum powder, is compressed into a pellet having an anode lead (lead 28 for anode 12 and lead 30 for anode 14) embedded therein and extending there from, and sintered under a vacuum at high temperatures. The porous body is then anodized in a suitable electrolyte to fill its pores with electrolyte and form a continuous dielectric oxide film on the sintered body. A preferred tantalum material and method of manufacturing an anode pellet for the present capacitor 10 is described in U.S. Pat. No. 9,312,075 to Liu et al., which is assigned to the assignee of the present invention and incorporated herein by reference.

In particular, the anode pellets 12, 14 and their leads 28, 30 are anodized by immersing the pellet/lead assembly in an electrolyte and applying a current. The anodizing electrolyte includes constituents such as water and phosphoric acid and perhaps other organic solvents. The application of current drives the formation of an oxide film that is proportional in thickness to the targeted forming voltage. A pulsed formation process may be used where current is cyclically applied and removed to allow diffusion of heated electrolyte from the internal pores of the anode. Intermediate washing and annealing steps may be performed to facilitate formation of a stable, defect free oxide. Preferably, the anode leads 28, 30 comprise the same material as the anodes 12, 14, and the anode pellet/lead assembly is anodized to a formation voltage that is greater than zero up to 550 V.

Further, cathode active material 16 is directly contacted to the inner surface of the first casing member face wall 20A and on both sides of the second casing member face wall 22A. Cathode active material 16 is also contacted to an inner surface of the cover plate 26. Preferably the various cathode active material 16 coatings have a thickness of about a few hundred Angstroms to about 0.1 millimeters and are aligned in a face-to-face relationship with the immediately adjacent major faces of the anodes 12, 14. Alternatively, the cathode active material 16 is coated on a conductive substrate (not shown) in electrical contact with the inner surface of the first casing member face wall 20A, both sides of the second casing member face wall 22A, and the inner surface of the cover plate 26. In any event, the cathode active material 16 is preferably spaced from the respective sidewalls 20B, 20C, and 22B to 22E.

In that respect, the face walls 20A, 22A and cover plate 26 may be of an anodized-etched conductive material, have a sintered active material with or without oxide contacted thereto, or they may be contacted with a double layer capacitive material, for example a finely divided carbonaceous material such as graphite, carbon, activated carbon, platinum black, a redox, pseudocapacitive or an under potential material, or they may be an electroactive conducting polymer such as polyaniline, polypyrrole, polythiophene, and polyacetylene, and mixtures thereof.

According to one preferred aspect of the present invention, the redox or cathode active material 16 includes an oxide of a first metal, the nitride of the first metal, the carbon nitride of the first metal, and/or the carbide of the first metal, the oxide, nitride, carbon nitride, and carbide having pseudocapacitive properties. The first metal is preferably selected from the group consisting of ruthenium, cobalt, manganese, tantalum, iron, niobium, iridium, titanium, zirconium, hafnium, rhodium, vanadium, osmium, palladium, platinum, nickel, and lead.

The cathode active material 16 may also include a second or more metals. The second metal is in the form of an oxide, a nitride, a carbon nitride or a carbide, and is not essential to the intended use of the conductive face walls 20A, 22A and cover plate 26 as a capacitor electrode. The second metal is different than the first metal and is selected from one or more of the group consisting of tantalum, titanium, nickel, iridium, platinum, palladium, gold, silver, cobalt, molybdenum, ruthenium, manganese, tungsten, iron, zirconium, hafnium, rhodium, vanadium, osmium, and niobium. In a preferred embodiment of the present invention, the cathode active material 16 includes an oxide of ruthenium and is substantially devoid of the second or more metals.

The cathode active material 16 may also be selected from graphitic or glassy carbon on titanium carbide, carbon and silver vanadium oxide on titanium carbide, carbon and crystalline manganese dioxide on titanium carbide, platinum on titanium, ruthenium on titanium, barium titanate on titanium, carbon and crystalline ruthenium oxide on titanium carbide, carbon and crystalline iridium oxide on titanium carbide, silver vanadium oxide on titanium, and activated carbon.

As disclosed in U.S. Pat. No. 7,116,547 to Seitz et al., a preferred cathode material coating process is by pad printing. An ultrasonically generated aerosol, as described in U.S. Pat. Nos. 5,894,403, 5,920,455, 6,224,985, and 6,468,605, all to Shah et al., is also suitable for making a coating of the cathode active material 16. In that manner, the ultrasonically generated cathode active material contacted to the conductive surfaces of the casing conductive face walls 20A, 22A and the cover plate 26 has a majority of its particles with diameters of less than about 10 microns. This provides an internal surface area for the active material of about 10 $m^2$/gram to about 1,500 $m^2$/gram. The Shah et al. '403, '455, '985 and '605 patents and the Seitz et al. '547 patent are assigned to the assignee of the present invention and incorporated herein by reference.

As shown in FIG. 2, to prevent an internal electrical short circuit between the electrodes, a first separator envelope 34 of electrically insulative material surrounds the first anode 12. Similarly, a second separator envelope 36 of electrically insulative material surrounds the second anode 14. The separator envelopes 34, 36 prevent direct physical contact of the respective anodes 12, 14 with the facing cathode active materials 16 while allowing for ionic transport during charging and discharging of the capacitor 10. The respective separator envelopes 34, 36 are of materials that are chemically unreactive with the anode and cathode active materials and both chemically unreactive with and insoluble in the electrolyte.

Illustrative separator materials include woven and non-woven fabrics of polyolefinic fibers including polypropylene and polyethylene, or fluoropolymeric fibers including polyvinylidene fluoride, polyethylenetetrafluoroethylene, and polyethylenechlorotrifluoroethylene laminated or superposed with a polyolefinic or fluoropolymeric microporous film, non-woven glass, glass fiber materials and ceramic materials. Suitable microporous films include a polyethylene membrane commercially available under the designation SOLUPOR®, (DMS Solutech); a polytetrafluoroethylene membrane commercially available under the designation ZITEX®, (Chemplast Inc.) or EXCELLERATOR®, (W.L. Gore and Associates); a polypropylene membrane commercially available under the designation CELGARD®, (Celgard LLC); and a membrane commercially available under the designation DEXIGLAS®, (C. H. Dexter, Div., Dexter Corp.). Cellulose based separators also typically used in capacitors are contemplated by the scope of the present invention. Depending on the working electrolyte, the material used for the envelopes 34, 36 can be treated to improve its wettability, for example with a surfactant, as is well known by those skilled in the art. The working electrolyte will be described in detail hereinafter, The capacitor 10 illustrated in FIGS. 1 and 2 further includes an insulator and seal structure, for example a glass-to-metal seal, for each of the anodes 12, 14 and their leads 28, 30. The respective insulator and seal structures are designated 38 and 40 in the drawings. As is well known to those skilled in the art, the insulator and seal structures 38 and 40 comprise an insulative glass 42 that provides a hermetic seal between the inside of a ferrule 44 supported by the casing members 20, 22 and the anode leads 28, 30. The insulative glass 42 is, for example, ELAN® type 88 or MANSOL™ type 88. In that manner, those portions of the anode leads 28, 30 extending outside the casing 18 are hermetically sealed from the interior thereof to electrically isolate the leads from the casing members 20, 22 serving as the terminal for the cathode electrode. The ferrules 44 for the respective insulator and seal structures 38, 40 are configured for mounting is a suitably sized opening in a sidewall of the casing members 20, 22.

Alternatively, the insulator and seal structures 38, 40 do not have glass isolating the leads 28, 30 from the respective ferrules 44. Instead, the insulative material 42 is a synthetic elastomeric material that is configured to seal between feedthrough leads 28, 30 and their ferrules 44. A suitable synthetic elastomeric material is, for example, Master-Sil 151 made by Master Bond. While such a seal structure using only a synthetic polymeric material is not necessarily hermetic, acceptable isolation of the working electrolyte from inside the stacked casing members 20, 22 to outside the casing 18 is provided.

To complete the capacitor 10, a working electrolyte (not shown) is filled into the first and second capacitor enclosures to contact the anode 12, 14 and cathode active materials 16. A suitable working electrolyte for the capacitor 10 is described in U.S. Pat. No. 6,219,222 to Shah et al., which includes a mixed solvent of water and ethylene glycol having an ammonium salt dissolved therein. U.S. Patent Pub. Nos. 2003/0090857 and 2003/0142464 describe other working electrolytes for the present capacitor 10. The working electrolyte of the former publication comprises water, a water-soluble inorganic and/or organic acid and/or salt, and a water-soluble nitro-aromatic compound while the latter relates to a working electrolyte having de-ionized water, an organic solvent, isobutyric acid and a concentrated ammonium salt. These publications and patent are assigned to the assignee of the present invention and incorporated herein by reference.

Regardless its constituents, the working electrolyte is provided inside the hermetically sealed capacitor enclosures through respective fill openings, each opening closed by a hermetic closure 46 and 48, as is well known by those skilled in the art.

As shown in FIG. 1, the anode leads 38, 40 for capacitor 10 are unconnected from each other so that the respective anodes 12, 14 can be charged independently. This could take the form of charging one of the anodes partially or completely to a rated voltage, and then charging the other anode. In other situations, it might be preferred to charge one anode at a rate different than that at which the other anode is charged. For example, a pulse current could charge one of the anodes while the other is done by constant power charging. An advantage of separately connecting the anode leads 28, 30 to an external charging circuit is that charging and discharging currents can be distributed over the anodes 12, 14, which allows smaller, more flexible leads 38, 40 and connections than one lead with an equivalent current carrying capacity.

Alternatively, FIG. 2 illustrates that the anodes 12, 14 can be connected to a common polarity terminal. In that manner, the respective anode leads 28 and 30 are electrically connected to a common positive polarity terminal 50. This is accomplished by first mounting an insulator 52 having spaced apart openings sized to receive the leads 28, 30. A bridge 54 of conductive material, for example, nickel, is then supported on the insulator 52. The bridge 54, which has a pair of openings that receive the anode leads 28, 30, is secured to these leads by respective welds, preferably by laser welds, (not shown) to electrically connect the leads together in parallel. Finally, the common positive terminal 50 is electrically connected to bridge 54. The bridge 54 can also be crimped onto the leads 28, 30 by applying a force that deforms the bridge from opposed directions.

In use, the capacitor 10 is connected to a load (not shown) as a power source. That can be done by either connecting the leads 28, 30 or the negative polarity terminal pin 50 to the load. A common positive terminal pin 56 (FIG. 1) connected to the casing 18 is also connected to the load to complete the electrical connection.

While not shown in the drawings, a molded polymeric cradle or restraint is preferably provided for containing the anodes 12, 14 in the desired position inside the capacitor enclosure should the capacitor 10 experience high shock and vibration conditions. Suitable restraints are described in U.S. Pat. No. 7,085,126 to Muffoletto et al. and U.S. Pat. No. 7,092,242 to Gloss et al., which are assigned to the assignee of the present invention and incorporated herein by reference.

Figure 3:
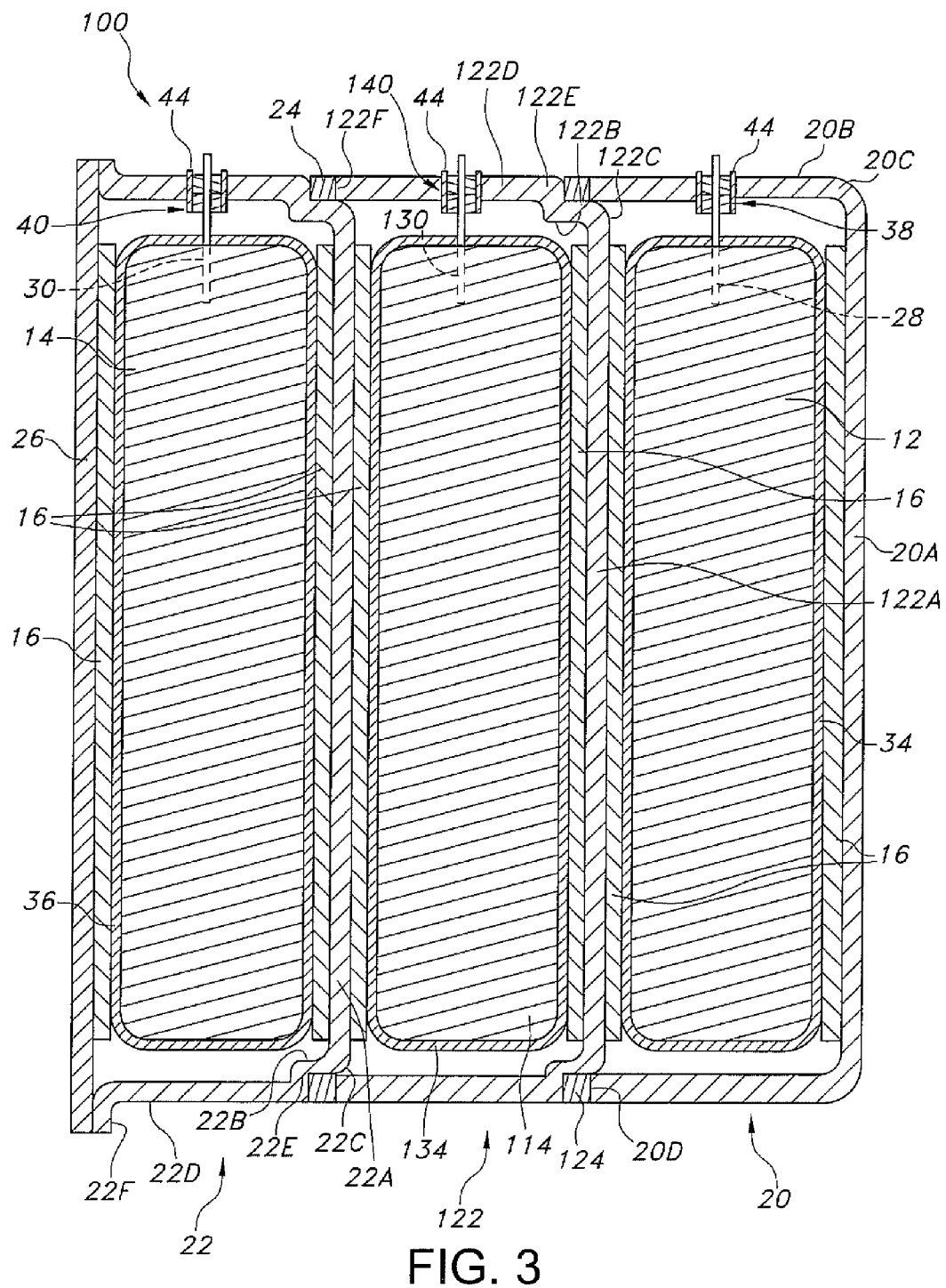
FIG. 3 is a partially broken-away view illustrating another casing embodiment for a three anode capacitor according to the present invention.

It should be understood that the capacitor 10 of the present invention is not limited to dual anode designs. FIG. 3 is a cross-sectional view of another embodiment of a capacitor 100 according to the present invention. Capacitor 100 includes a third casing member 122 stacked between or intermediate the first and second casing members 20 and 22. The third casing member 122 is similar to the second casing member 22 and comprises a face wall 122A joined to a minor surrounding or annular sidewall 122B by a first annular curved sidewall 122C. The minor surrounding sidewall 122B is joined to a major surrounding or annular sidewall 122D by an outwardly extending annular step 122E. The major surrounding sidewall 122D extends to an outwardly projecting annular rim 122F defining an open end for the casing member 122.

The annular step 122E between the minor and major surrounding sidewalls 122B, 122D of the third or intermediate casing member 122 is sized and shaped to receive the upper edge 20D of the first casing member 20 stacked therein. Similarly, the annular step 22E between the minor and major surrounding sidewalls 22B, 22D of the second casing member 22 is sized and shaped to receive the upper edge 122F of the intermediate casing member 122. The first, second and third casing members 20, 22 and 122 stacked together in this manner are secured to each other by annular welds 24 and 124, preferably laser welds. When stacked and secured together, the third casing member 122 closes the first casing member 20 and the second casing member 22 closes the third casing member 122 with the respective sidewalls 22D, 122D and 20B substantially aligned with each other.

A third anodized anode 114 including an extending lead 130 and cathode active material 16 supported on walls 22A and 122A is housed in the capacitor enclosure of the third casing member 122. The anode and cathode materials are prevented from contacting each other by a separator envelope surrounding the anode 114. The anode 114 and cathode 16 are contacted by a suitable working electrolyte and a seal and insulator structure, similar to those previously described, electrically isolates the lead 130 from the equipotential casing members 20, 120 and 22 closed by the cover 26. Finally, FIG. 3 illustrates that the respective anode leads 28, 30 and 130 are unconnected from each other. However, that is by way of example only. If desired, those leads can be electrically connected in parallel as described for leads 28 and 30 with respect to FIG. 2.

Moreover, while the capacitor 100 embodiment shown in FIG. 3 has three stacked casing members 20, 22 and 122 closed by a cover plate 26, which is by way of example only. Those skilled in the art will readily understand that a fourth, fifth and more casing members housing a respective anode and cathode can be stacked between the first and second casing members 20 and 22. The number is only limited by the particular application in which the capacitor is intended to be used as a power source.

Although several embodiments of the invention have been described in detail, for purposes of illustration, various modifications of each may be made without departing from the spirit and scope of the invention. Accordingly, the invention is not to be limited, except as by the appended claims.

What is claimed is:

1. A capacitor, which comprises:
   a) a casing comprising:
      i) a first casing member comprising a first face wall extending to a first surrounding sidewall, the first surrounding sidewall extending to a first annular edge defining a first open end;
      ii) a second casing member comprising a second face wall extending to a second surrounding sidewall, the second surrounding sidewall extending to a second annular edge defining a second open end, wherein the second casing member is supported on the first annular edge to close the first open end of the first casing member and thereby provide a first capacitor enclosure comprising the first and second casing members in a stacked relationship; and
      iii) a cover secured to the second annular edge to close the second open end of the second casing member and thereby provide a second capacitor enclosure; and
   b) a cathode active material residing in electrical contact with:
      i) at least one of the first face wall and the second face wall inside the first capacitor enclosure; and
      ii) at least one of the second face wall and the cover inside the second capacitor enclosure;
   c) at least one anode residing in each of the first and second capacitor enclosures and facing the cathode active material;
   d) a separator intermediate the anode and cathode in both of the first and second capacitor enclosures;
   e) a first insulative seal supported by the first casing member and a second insulative seal supported by at least one of the second casing member and the cover to electrically insulate a respective first lead for the first anode housed in the first capacitor enclosure and a second lead for the second anode housed in the second capacitor enclosure from the casing serving as a terminal for the cathode active material; and
   f) a working electrolyte provided in the first and second capacitor enclosures in contact with the first and second anodes and the cathode active material.

2. The capacitor of claim 1 wherein an inwardly extending annular step resides between the second face wall and the second surrounding sidewall, and wherein the first annular edge of the first casing member is received in the inwardly extending annular step to close the first open end of the first casing member and thereby provide the first capacitor enclosure comprising the first and second casing members in the stacked relationship.

3. The capacitor of claim 1 wherein:
   i) the first insulative seal comprises a first ferrule supported by the first casing member; and
   ii) the second insulative seal comprises a second ferrule supported by at least one of the second casing member and the cover,
   iii) wherein at least one of the first and second ferrules supports a sealing glass contacting the respective first and second anode lead.

4. The capacitor of claim 1 wherein:
   i) the first insulative seal comprises a first ferrule supported by the first casing member; and
   ii) the second insulative seal comprises a second ferrule supported by at least one of the second casing member and the cover,
   iii) wherein at least one of the first and second ferrules supports a polymeric material, but not a sealing glass, contacting the respective first and second anode lead.

5. The capacitor of claim 1 wherein the cover is a planar, plate shaped member aligned substantially parallel to the first and second face walls of the first and second casing members.

6. The capacitor of claim 1 wherein the second surrounding sidewall of the second casing member includes an outwardly extending annular rim leading to the second annular edge, and the cover is supported on the annular rim.

7. The capacitor of claim 1 wherein the first and second anodes are sintered tantalum pellets that are characterized as having been anodized to a formation voltage that is greater than zero up to 550 V.

8. The capacitor of claim 1 wherein the cathode active material is selected from the group consisting of ruthenium, cobalt, manganese, molybdenum, tungsten, tantalum, iron, niobium, iridium, titanium, zirconium, hafnium, rhodium, vanadium, osmium, palladium platinum, nickel, lead, gold, silver, cobalt, and mixtures thereof.

9. The capacitor of claim 1 wherein the anode is selected from the group consisting of tantalum, aluminum, titanium, niobium, zirconium, hafnium, tungsten, molybdenum, vanadium, silicon, germanium, and mixtures thereof.

10. The capacitor of claim 1 wherein in the stacked relationship, the first and second surrounding sidewalls of the first and second casing members are substantially aligned with each other.

11. The capacitor of claim 1 wherein the first anode in the first capacitor enclosure is intermediate and facing the cathode active material contacted to an inner surface of the first face wall of the first casing member and an outer surface of the second face wall of the second casing member, and wherein the second anode in the second capacitor enclosure is intermediate and facing the cathode active material contacted to an inner surface of the second face wall of the second casing member and an inner surface of the cover.

12. The capacitor of claim 1 wherein the first casing member is welded to the second casing member to provide the first capacitor enclosure, and the cover is welded to the second casing member to provide the second capacitor enclosure.

13. The capacitor of claim 1 wherein the first and second anodes are electrically connected in parallel outside the casing.

14. A capacitor, which comprises:
a) a casing comprising:
   i) a first casing member comprising a first face wall supporting a first surrounding sidewall, the first surrounding sidewall extending to a first annular edge defining a first open end;
   ii) a second casing member comprising a second face wall extending to a second surrounding sidewall, the second surrounding sidewall extending to a second annular edge defining a second open end, wherein the second casing member is supported on the first annular edge to close the first open end of the first casing member and thereby provide a first capacitor enclosure comprising the first and second casing members in a stacked relationship;
   iii) a third casing member comprising a third face wall extending to a third surrounding sidewall, the third surrounding sidewall extending to a third annular edge defining a third open end, wherein the third casing member is supported on the second annular edge to close the second open end of the second casing member and thereby provide a second capacitor enclosure comprising the second and third casing members in a stacked relationship; and
   iv) a cover secured to the third annular edge to close the third open end of the third casing member and thereby provide a third capacitor enclosure; and
b) a cathode active material residing in electrical contact with:
   i) at least one of the first face wall and the second face wall inside the first capacitor enclosure;
   ii) at least one of the second face wall and the third face wall inside the second capacitor enclosure;
   iii) at least one of the third face wall and the cover inside the third capacitor enclosure; and
c) at least one anode residing in each of the first, second and third capacitor enclosures and facing the cathode active material;
d) a separator intermediate the anode and cathode in the first, second and third capacitor enclosures;
e) a first insulative seal supported by the first casing member, a second insulative seal supported by at least one of the second casing member and the third casing member, and a third insulative seal supported by at least one of the third casing member and the cover to electrically insulate a respective first lead for the first anode housed in the first capacitor enclosure, a second lead for the second anode housed in the second capacitor enclosure, and a third lead for the third anode housed in the third capacitor enclosure from the casing serving as a terminal for the cathode active material; and
f) a working electrolyte provided in the first, second and third capacitor enclosures in contact with the first, second and third anodes and the cathode active material.

15. The capacitor of claim 14 wherein:
i) a second inwardly extending annular step resides between the second face wall and the second surrounding sidewall with the first annular edge of the first casing member being received in the second inwardly extending annular step to close the first open end of the first casing member and thereby provide the first capacitor enclosure comprising the first and second casing members in the stacked relationship; and
ii) a third inwardly extending annular step resides between the third face wall and the third surrounding sidewall with the second annular edge of the second casing member being received in the third inwardly extending annular step to close the second open end of the second casing member and thereby provide the second capacitor enclosure comprising the second and third casing members in the stacked relationship.

* * * * *